(12) United States Patent
Freudenberger et al.

(10) Patent No.: US 8,403,560 B2
(45) Date of Patent: Mar. 26, 2013

(54) COMPUTED TOMOGRAPHY SYSTEM WITH LIQUID COOLING

(75) Inventors: Joerg Freudenberger, Kalchreuth (DE); Ernst Neumeier, Aurachtal (DE); Lothar Werner, Weissenohe/Dorfhaus (DE)

(73) Assignee: Siemens Aktiengesellschaft, Munich (DE)

( * ) Notice: Subject to any disclaimer, the term of this patent is extended or adjusted under 35 U.S.C. 154(b) by 180 days.

(21) Appl. No.: 13/076,738

(22) Filed: Mar. 31, 2011

(65) Prior Publication Data
US 2011/0243296 A1    Oct. 6, 2011

(30) Foreign Application Priority Data
Mar. 31, 2010    (DE) .......................... 10 2010 013 604

(51) Int. Cl.
*H01J 35/10*    (2006.01)
(52) U.S. Cl. ........................................ 378/200; 378/141
(58) Field of Classification Search .............. 378/4, 130, 378/141, 199–200
See application file for complete search history.

(56) References Cited

U.S. PATENT DOCUMENTS

| | | | |
|---|---|---|---|
| 6,366,642 B1 * | 4/2002 | Andrews ........................ | 378/130 |
| 6,904,128 B2 | 6/2005 | Schlögl et al. | |
| 7,221,736 B2 * | 5/2007 | Heidrich et al. .............. | 378/141 |
| 7,302,042 B2 * | 11/2007 | Hansen et al. ................. | 378/141 |
| 2004/0028185 A1 * | 2/2004 | Schlogl et al. ................. | 378/141 |

* cited by examiner

*Primary Examiner* — Hoon Song
(74) *Attorney, Agent, or Firm* — Schiff Hardin LLP

(57) ABSTRACT

A computed tomography system has a gantry with a rotor side that can be rotated around a system axis during operation, at which at least one x-ray tube is mounted. To cool the at least one x-ray tube a liquid cooling system is equipped with a fluid volume filled with cooling liquid, the fluid volume extends over distances of different sizes from the system axis. The fluid volume is located on the rotor of the gantry and thus is exposed to centrifugal force during operation. To increase pressure in the cooling system, a flexible compensation volume and a movable mass element that rotate with the gantry are provided. The mass element is arranged such that the centrifugal force acting on the mass element during operation causes pressure to be exerted on the cooling liquid.

12 Claims, 4 Drawing Sheets

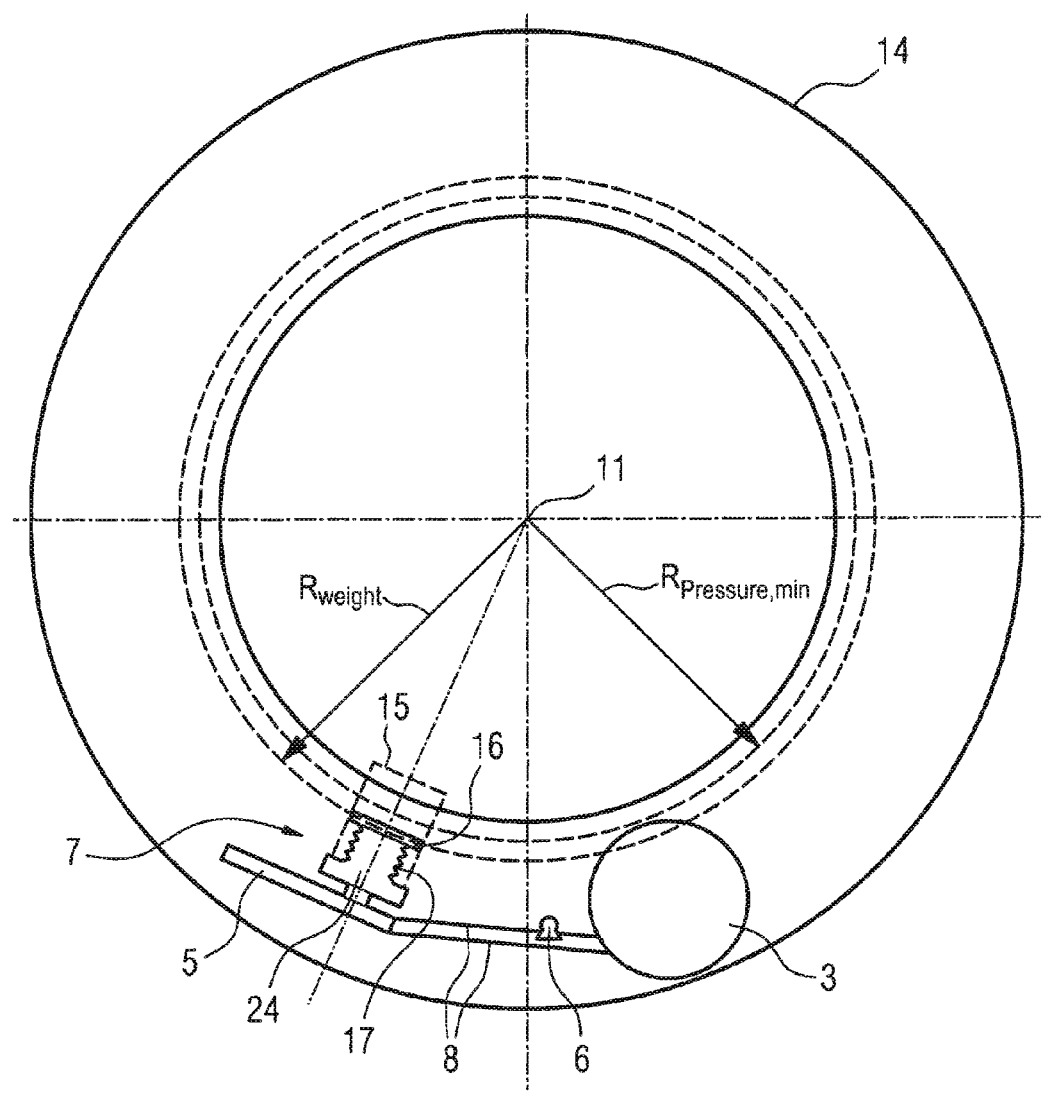

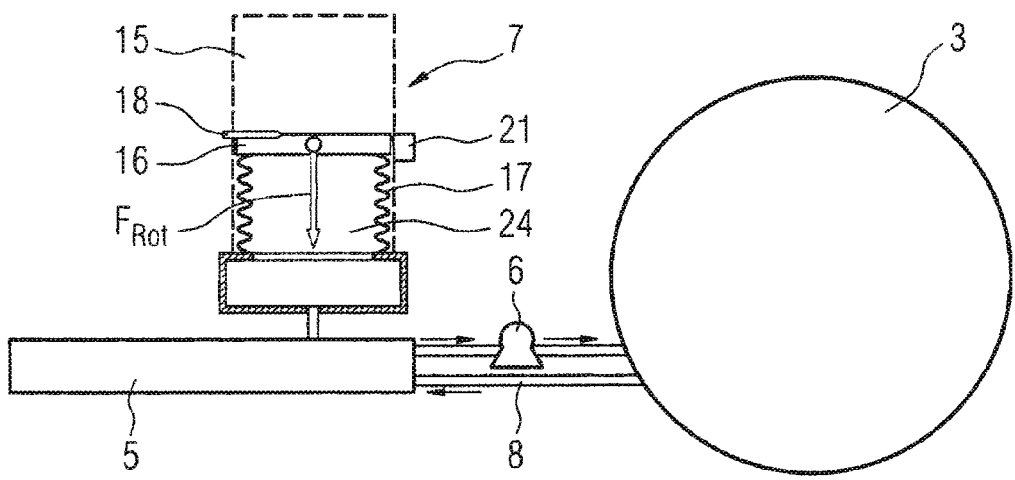
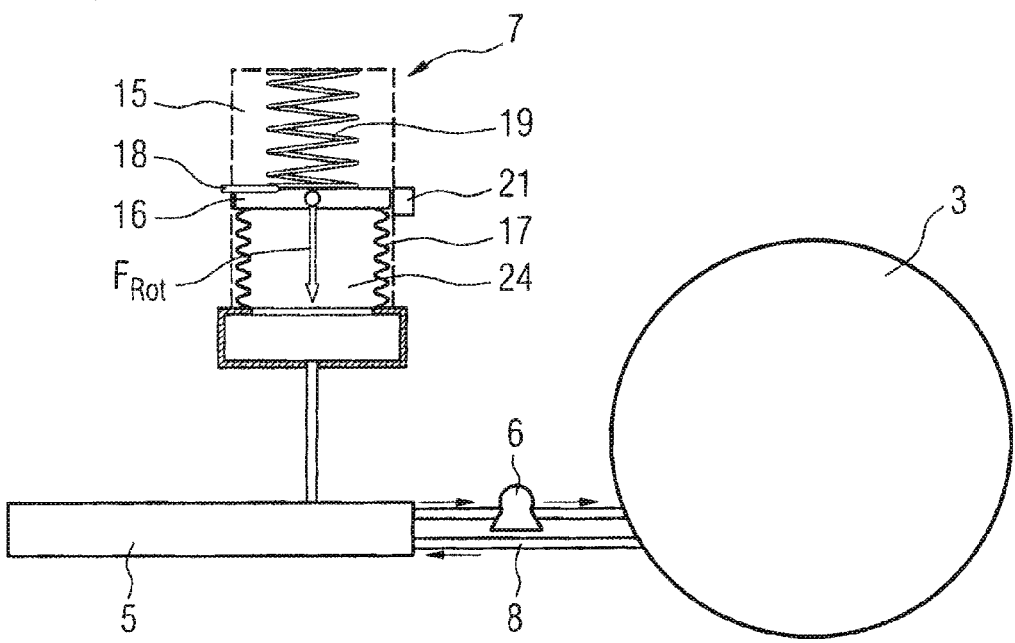

COMPUTED TOMOGRAPHY SYSTEM WITH LIQUID COOLING

BACKGROUND OF THE INVENTION

1. Field of the Invention

The present invention concerns a computed tomography system (CT system) of the type having at least one rotor in a gantry that in operation can be rotated around a system axis, on which rotor side is arranged at least one x-ray tube cooled by a liquid cooling system equipped with a liquid volume filled with coolant liquid, which liquid volume extends over distances of varying length from the system axis and is located on the rotor of the gantry that is exposed to centrifugal force in operation.

2. Description of the Prior Art

In x-ray tubes more than 99% of the energy used is converted into heat in the generation of x-ray radiation. This heat is discharged from the x-ray tube with the use of a coolant. In x-ray tubes for computed tomography the coolant circuit is subjected to centrifugal forces at the rotor of the gantry that rotates in the CT system, since the at least one x-ray tube is also arranged at the gantry, so that pressure differences arise in the cooling system. The lowest pressure is at the point in the radiator system that is located at the smallest radius in the CT system, and thus is exposed to the lowest centrifugal forces. The exit window of the x-ray tube (which must be cooled particularly well) is typically located optimally close to the patient or to the rotation center of the gantry in order to provide sufficient dose output. Water or anticorrosion or antifreeze agents are normally used as coolants to cool the x-ray tube, as well as the exit window of the x-ray tube. If the coolant temperature in the region of high heat transfer rises to the boiling point, the fluid vaporizes and the heat transport is interrupted. The boiling temperature depends on the pressure, such that higher temperatures can also be allowed at a higher pressure without boiling of the coolant fluid occurring. However, a pressure gradient exists in the rotating gantry due to the centrifugal force increasing away from the rotation center, and decreasing toward the rotation center, such that the pressure near the rotation center (thus in the region of the exit window that is severely thermally charged) is particularly low. A tendency toward bubble formation in this region can be counteracted only by measures to increase pressure.

An additional problem is that expansion occurs with the heating of the coolant, such that an expansion vessel or measures with similar function are necessary in order to prevent destruction of the cooling system due to the expansion of the coolant.

In principle, two different cooling system technologies are known, namely pressure-less systems, as are described in the WO2007/127939 A2. For example, in such a system a membrane is used that is shifted upon expansion of the coolant medium. However, in this technique the pressure of the system identical to the environment pressure, which leads—as described above—to relatively low boiling temperatures, or makes it necessary to use special coolants with a high boiling point. Another embodiment of the cooling system for x-ray tubes in CT systems are known as closed (sealed) cooling systems, in which a boundary surface is charged with a force (for example a mechanical elastic tension or a pressure from a sealed gas volume or shock absorber), as described in U.S. Pat. No. 7,221,736 B2, for example. Due to the expansion of the coolant with increasing temperature, the counter-force at the membrane is increased and the pressure in the system likewise rises with increasing temperature.

A problem in the last variant of the known closed cooling system is that a new adjustment of the pressure by service technicians with special tools is necessary after exchanging a part of the cooling system (for example the radiator or the heat exchanger), and achieving a correct setting proves to be relatively difficult and has a certain tendency to error.

SUMMARY OF THE INVENTION

An object of the invention is to provide a cooling system for x-ray tubes of a CT system that can operate by pressure charging with simple coolants such as water or a mixture of water and anticorrosion or antifreeze agents, and that does not need any readjustment in the event of an exchange of parts belonging to the cooling system, and thus is less error-prone.

The invention is based on the insight that it is possible to adjust the pressure in the cooling system in a simple manner in operation, even without precise adjustments of elastic pressures or an overpressure in a two-chamber system, by using a mobile mass element rotating along with the gantry, this mass element being arranged relative to the fluid volume of the liquid cooling system so that the centrifugal force acting on the mass element during operation acts indirectly or directly on the coolant liquid and increases the pressure thereof. In principle, such an effect could also be achieved by the water column being extended in the direction of the rotation center point, but this is not feasible in a CT system since this region serves as a measurement (data acquisition) region and accordingly must remain open. Moreover, the radiator must be arranged as close as possible to the measurement region in order to achieve the desired fan angle.

For example, the action of the centrifugal force on a mass element at the cooling liquid can be achieved by the cooling liquid being partially bounded by a flexible membrane on which the mass element acts directly or indirectly. For example, such a membrane can be housed in a protuberance in a sight (inspection) glass and can be mounted within the sight glass at the side of the mass element (advantageously a material with high density) facing toward the rotation point, such that upon rotation the mass element compresses the membrane with the liquid. If the pressure should additionally be increased during the downtime of the gantry, an elastic element can additionally be mounted which exerts a desired base load of pressure on the membrane.

Such an embodiment has the advantage that a high flexibility with regard to the expansion response of the cooling liquid via heating and cooling is provided while at the same time practically no adjustment work at the pressure system is necessary if parts of the cooling system (for example the heat exchanger or pump groups) must be exchanged. At the same time, such a sight glass can also display the fluid level of the cooling liquid in a simple and certain manner.

Corresponding to these basic ideas, a CT system is improved by the invention, which CT system has:

at least one rotor in a gantry that, in operation, can rotate around a system axis, and at least one x-ray tube mounted at the rotor, a closed cooling system that cools the at least one x-ray tube, the closed liquid cooling system being equipped with a fluid volume that is filled with cooling liquid and extends over distances of varying length from the system axis, and a fluid volume located on the rotor of the gantry that is exposed to centrifugal force during operation.

The improvement of this CT system according to the invention is that a flexible compensation volume and a mobile mass element rotating with the gantry are provided, with the mass element arranged such that the centrifugal force acting on the mass element during operation exerts pressure on the cooling liquid.

The desired pressures in the cooling system automatically arise in relation to the rotation speed of the gantry by the use of such a device to generate pressure on the basis of centrifugal forces that occur at the gantry, without regulating adjustments of elastic forces or other pressure generators being necessary. In particular, this system is insensitive to possible fluctuations in the fill level due to thermal expansion or the exchange of components in the cooling system.

In an embodiment of the invention, a direct transfer of the centrifugal force of the mass element to the cooling liquid is provided. The possibility also exists to improve the effectiveness of the mass element by arranging it relatively far removed from the rotation center and to use a lever apparatus, a transmission or a hydraulic pressure transfer to transfer the centrifugal force of the mass element to the cooling liquid, for example. Given the application of such force-transferring elements, it must be ensured that the effect of the mass element is not lost due to the centrifugal force acting on the force transfer elements.

Furthermore, it is advantageous for the compensation volume to be bounded at least in part by a mechanically flexible membrane that is impermeable to the cooling liquid. Seals can possibly be foregone in such an embodiment.

Furthermore, the compensation volume can be located in a cylinder, with the mass element at least partially forming a displaceable piston in the cylinder, and with the cooling liquid present at a side of the cylinder whose volume communicates with the fluid volume.

As noted, to generate a predetermined base pressure an elastic element can be used with which pressure is exerted on the flexible compensation volume so that a defined minimum pressure is generated in the cooling liquid even during a downtime of the gantry. The elastic element can be arranged so as to exert its elastic force on the mass element. The mass element is fixed and, in the event of a downtime of the gantry, does not release "overhead" from the compensation volume due to the force of gravity.

In addition, given the use of such a cylinder a sensor can be arranged in a fluctuation region of the active surface, this sensor reacting to a variation of the fluid level and possibly triggering an alarm signal in the controller of the CT system.

The cylinder can be fashioned as a sight glass, and at least one marking or a marking range that indicates a correct fill level of the cooling liquid can be applied.

It is for the compensation volume to be provided with a ventilation device in which at least part the compensation volume is located, nearer to the system axis than to any other point in the fluid volume of the liquid cooling system. Since, if bubble formation does occur, it will most probably arise in the region of the lowest pressure, so this design ensures that bubble formation in principle will occur in the compensation vessel itself, which has appropriate ventilation capabilities, and bubble formation is avoided at the regions at which it could lead to problems in the heat transfer.

In order to achieve an optimally effective action of the mass element, it can have a higher specific density than the cooling liquid.

Furthermore, to simplify an exchange of components of the CT system that are integrated into the cooling system, at feast two components integrated into the cooling circuit of the CT system are connected with the cooling circuit via couplings that automatically seal themselves (advantageously at both ends) upon decoupling. An exchange of the components thus can be executed in a simple manner, so the components respectively retain their cooling liquid, or new components with a cooling liquid volume that is already filled are used.

BRIEF DESCRIPTION OF THE DRAWINGS

FIG. 2 is a cross section through a CT system in the region of the gantry.

FIG. 3 is a schematic representation of the liquid cooling system of a CT system without a spring.

FIG. 4 is a schematic representation of the liquid cooling system of a CT system with a spring.

DESCRIPTION OF THE PREFERRED EMBODIMENTS

Figure 1:
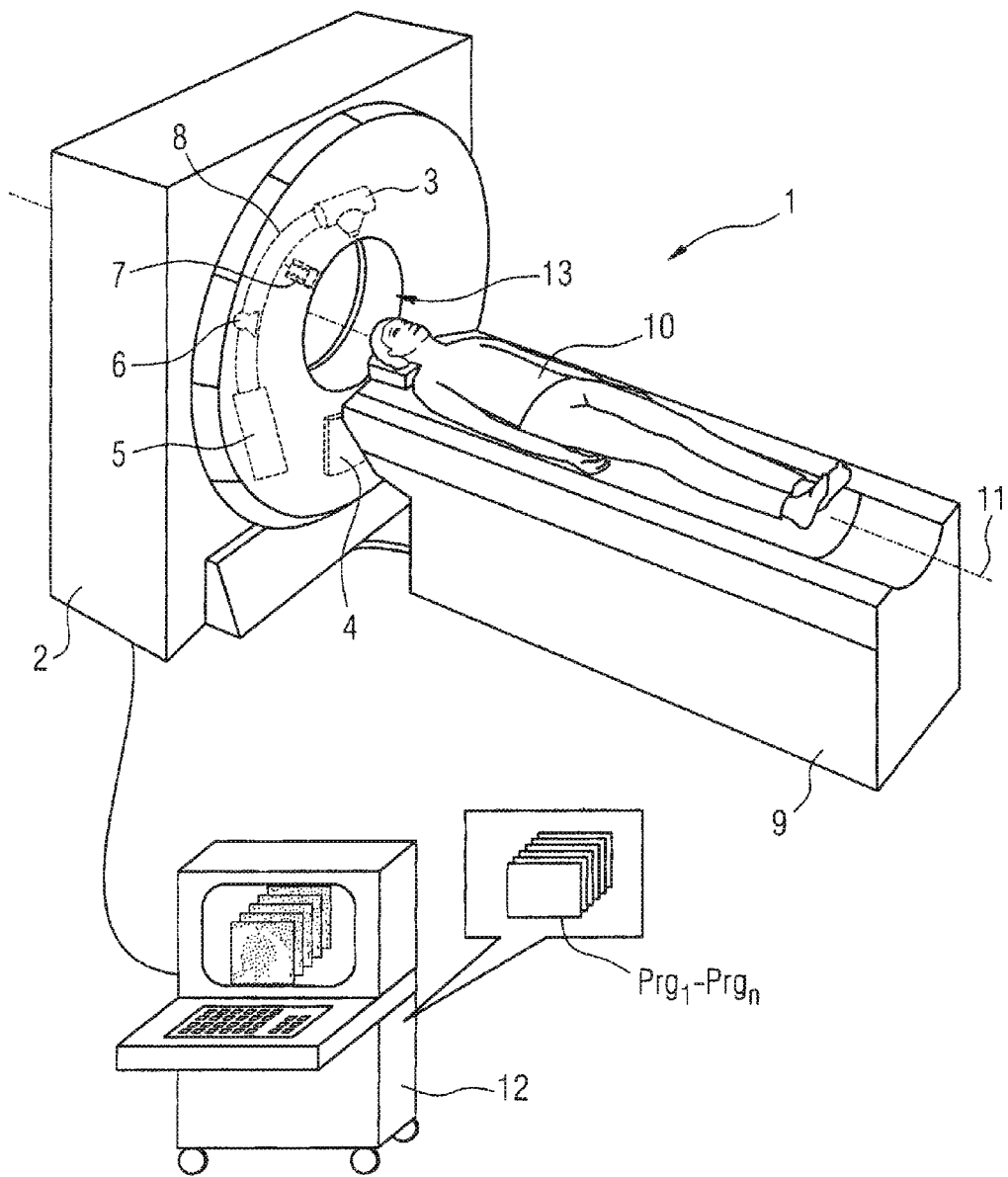
FIG. 1 is an overview presentation of a CT system.

In the following the invention is described in detail using the preferred exemplary embodiments with the use of figures, wherein only the features necessary to understand the invention are shown. The following reference characters and abbreviations are used: 1: CT system; 2: gantry housing; 3: x-ray radiator/x-ray tube; 4: detector; 5: heat exchanger; 6: coolant pump; 7: pressure generator; 8: coolant lines; 9: patient bed; 10: patient; 11: system axis; 12: control and computer system; 13: measurement field; 14: rotor; 15: sight glass; 16: mass element; 17: membrane; 18: marking; 19: elastic element; 20: self-sealing coupling; 21: sensor; 22: lever arm; 23: bearing; 24: compensation volume ; $F_{Rot}$: centrifugal force; $Prg_1$ through $Prg_n$: computer programs; $R_{Weight}$: radius of the mass element; $R_{Pressure,min}$: radius of the location with minimum pressure given a rotating gantry.

FIG. 1 shows a CT system 1 in three-dimensional representation with a gantry housing 2 which has a measurement field 13 through which a patient 10 can be shifted (with the aid of a displaceable patient bed 9) along the system axis 11 for examination. In this presentation a radiator/detector system arranged on the gantry is also shown schematically which consists of an x-ray radiator 3 and an opposing detector 4. The x-ray radiator 3 is connected via cooling lines 8 with a cooling system consisting of a heat exchanger 5 and a coolant pump 6 used to transport the coolant. According to the invention, this cooling system is also connected to a pressure generator 7 which is located at the rotating gantry, and with the aid of the centrifugal force occurring in the operation of the gantry the pressure in the cooling system increases in that a mass element allows the centrifugal force acting on the mass element to affect the liquid of the cooling system.

For completeness, a control and computer system 12 is also additionally shown which controls the functions of the CT system and conducts image reconstructions on the basis of the obtained detector data. For this computer programs $Prg_1$ through $Prg_n$ are recorded in memory, which computer programs are loaded and executed in the working memory of the computer system 12 as needed.

To depict the invention, in FIG. 2 a schematic section through the gantry region of a CT system is shown again, wherein here the depiction is limited only to the significant aspects of the cooling system. The cross section draws [sic] the rotor 14 of the gantry at which the x-ray radiator 3 is attached that is in turn connected with a heat exchanger 5 via a cooling line system 8. The transport of the coolant takes place via a coolant pump 6 located in the conduit system 8. To generate the desired overpressure, a device 7—hydraulically connected with the cooling system—to increase the static pressure is located in the coolant system. This device 7 here is basically composed of a mechanically flexible membrane that forms a compensation volume 24 in the form of a sack-like protuberance at which a mass element 16 is borne, such that in the case of a rotation of the rotor 14 of the gantry this mass element 16 attempts to compress—with its centrifugal force—the membrane and the fluid volume located in the membrane, which fluid volume is connected hydraulically with the cooling system. The membrane 17 and the mass element 16 are located in a cylindrical structure, for example a sight glass 15 through which the fluid level of the cooling system can be observed either via inspection or via correspondingly arranged sensors.

For information, in FIG. 2 the radius $R_{Weight}$ of the mass element is additionally plotted against the radius $R_{Pressure,min}$ that corresponds to the location of the cooling system that has the smallest distance from the rotation center (thus from the system axis 11).

In principle, the locations that are nearest the rotation center are also simultaneously the locations at which—in the case of a bubble formation in the cooling system—these bubbles would collect. However, with the use of the device 7 the pressure in the cooling circuit should be increased such that a bubble formation does not arise. At the same time, however, this system should also be designed such that a complicated adjustment—as is typical in the prior art—does not need to take place; rather, a desired pressure is generated based simply on the existing physical conditions due to the rotation of the rotor of the gantry and essentially independent of the fill level in the cooling system. This is achieved by the magnitude of the pressure in the cooling system being determined (caused) only by the centrifugal force acting on the mass element, such that adjustments of elastic forces or the like are no longer necessary.

FIG. 3 shows an excerpt of the cooling system in schematic representation. FIG. 3 shows an x-ray tube 3 that is connected via cooling lines 8 to a cooling system with a heat exchanger 5, with a pump 6 is integrated into the cooling lines. The pump 6 is responsible for the circulation of the cooling liquid. Furthermore, the device 7 according to the invention is connected to the cooling system, and the device 7 generates a predefined pressure increase in the cooling circuit via the action of centrifugal force. The device 7 includes a protuberance of the fluid volume forming a compensation volume 24, this fluid volume being bounded by a mechanically flexible membrane 17. The membrane 17 is loaded by a mass element 16 as soon as the rotor of the gantry begins to rotate. Both are arranged in a cylindrical sight glass 15 at which a marking 18 is provided with which the fill level of the cooling fluid can be visually observed without difficulty. As an alternative or in addition to the marking 18, a sensor 21 can be provided that (for example) detects the orientation of the mass element 16 and determines the fill level of the cooling fluid, or detects a deviation of the fill level.

It is advantageous for the mass element 16 to have a high specific density so that a relatively compact mass element can be used that is advantageously located within the sight glass or the cylindrical hollow space in which the protuberance of the fluid volume with the bounding membrane 17 is also located. This arrangement produces large pressure increases in the cooling system corresponding to the prevailing centrifugal force.

FIG. 4 shows the same situation as FIG. 3, but in the sight glass 15 an elastic element 19 is additionally arranged. Thus, given an "overhead" standstill, for example, thus when the vector of the centrifugal force is opposite the force of gravity prevents the mass element 16 from falling downwardly, but instead it is pressed with a certain bias pressure against the membrane 17. It should also be noted that both in FIG. 3 and in FIG. 4 the rotation center point of the system is arranged above the figures, such that given a rotation a centrifugal force $F_{Rot}$ is directed outwardly, and therefore the mass element 16 presses downwardly in relation to the drawing.

As mentioned, it is advantageous for the mass element 16 to have an optimally high specific density in order to be able to generate sufficient pressure in the cooling system given a small structural size. Due to very cramped space relationships in the region of the rotor of the gantry, it can be particularly advantageous when the pressure-generating device is not arranged to the side of the rotation center but rather is arranged at the outlying side relative to the rotation center. Furthermore, it can be advantageous for a sufficiently high pressure is generated with relatively small mass, such that the total rotating mass remains optimally low.

Figure 5:
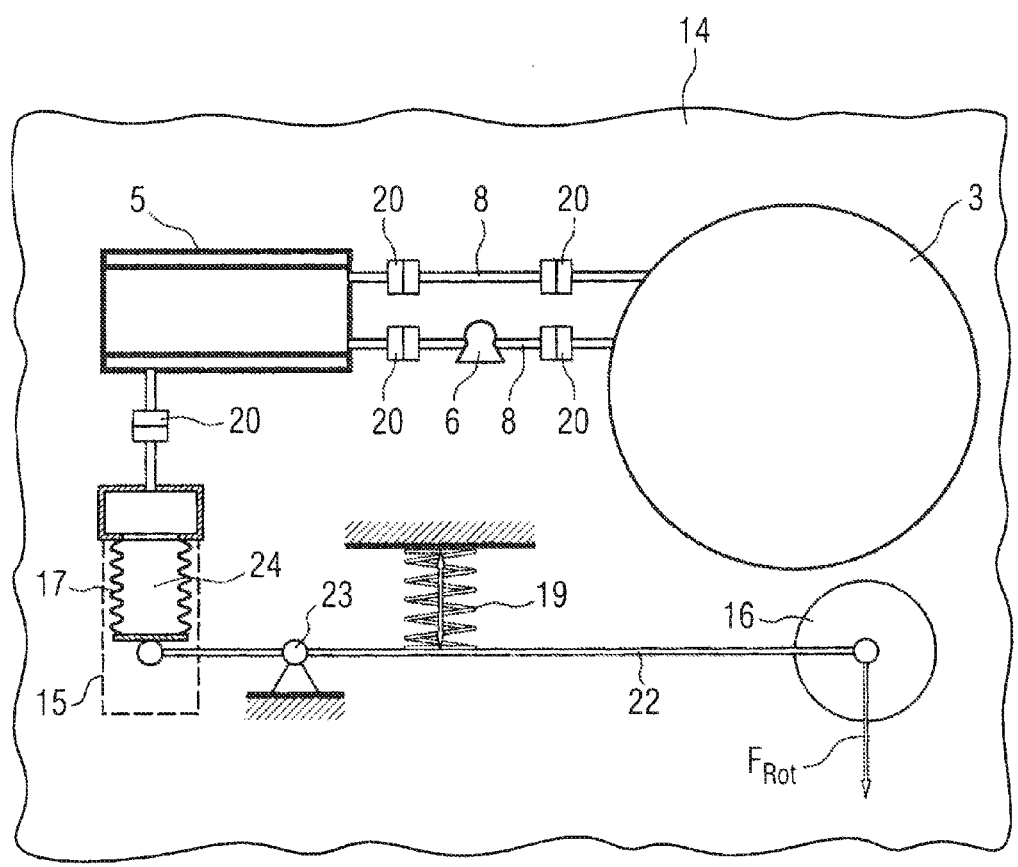
FIG. 5 is a schematic representation of a segment rotor of the gantry with device to increase pressure utilizing the lever action.

An embodiment that satisfies these particular requirements is shown in FIG. 5. This shows a segment from the rotor of the gantry in the region of the cooling system and the x-ray radiator 3. This x-ray radiator 3 here is also connected via cooling lines 8 with a heat exchanger 5 that is in turn connected with its fluid volume with a device 7 to generate an additional pressure with the aid of the occurring centrifugal force, which here however is arranged at the side of the rotating part of the gantry 14 that faces away from the rotation point.

By the use of a lever, a high internal pressure in the cooling system can hereby also be generated with the aid of a relatively low weight of a mass element 16 via the existing centrifugal force. In the embodiment shown here, the mass element 16 is arranged on the long side of a lever arm 22. The lever arm is supported by a bearing 23 so that the centrifugal force acting at the mass element 16 is transferred with a corresponding translation to the membrane 17 or the compensation volume 24, and thus to the cooling fluid.

It should be noted that, within the scope of the invention, not only a lever mechanism is shown, but also equivalent different mechanical translation mechanisms (for example via rotation elements of different sizes) can be used, or hydraulic translations.

Here in the embodiment of FIG. 5 an additional elastic element 19 is optionally shown which—for example—can engage with the lever arm 22 in order to generate a specific base pressure at the fluid.

Within the scope of the present invention, self-sealing couplings 20 can be provided in the region of the hydraulic compounds of the individual elements of the cooling system. The self-sealing couplings 20 enable a component of the cooling system to be exchanged in a simple manner without having to implement a complete re-filling of the cooling system.

It is noted that, in the invention described herein and in particular the embodiments specifically shown, volume changes in fact lead to a variation of the level of the cooling liquid in a compensation volume across a relatively large range, but this change is completely decoupled from the pressure charge exerted on the compensation volume by the centrifugal force. The magnitude of the additionally generated pressure due to the device according to the invention depends only on the constants (determined by design) of the mass of the mass element (possibly affected by an amplification system by the action of the lever), the area of the pressure transfer to the cooling liquid system and the rotation speed of the gantry. Adjusting pressure settings as are necessary in the prior art can therefore be omitted.

Overall, the invention results in a CT that has a cooling device whose internal pressure no longer needs to be regulated by complicated adjustment tasks; rather, its internal pressure is adjusted via physical conditions that do not need any readjustment. The exchange of individual components—advantageously with the assistance of self-sealing couplings—is therefore also simple to accomplish.

Although modifications and changes may be suggested by those skilled in the art, it is the intention of the inventors to embody within the patent warranted hereon all changes and modifications as reasonably and properly come within the scope of their contribution to the art.

We claim as our invention:

1. A computed tomography system, comprising:
   a gantry comprising a stationary part and a rotor that rotates, relative to said stationary part, around a system axis;
   an x-ray tube mounted to said rotor;
   a closed liquid cooling system in thermal communication with said x-ray tube that cools said x-ray tube, said closed liquid cooling system comprising a fluid volume filled with cooling liquid, said fluid volume comprising respective portions located at different distances from said system axis;
   said fluid volume being located at said rotor and being exposed to centrifugal force during rotation of said rotor, said fluid volume comprising a compensation volume that changes in size dependent on a force acting thereon; and
   a mass element movably mounted on said rotor that moves due to said centrifugal force acting on said mass element during rotation of said rotor, said mass element mechanically interacting with said compensation volume to impart said force to said compensation volume in response to the centrifugal force acting on the mass element, to change said volume size of said compensation volume to exert pressure on said cooling liquid.

2. A computed tomography system as claimed in claim 1 wherein said mechanical connection between said mass element and said compensation volume directly transfers said centrifugal force to exert said pressure on said cooling liquid.

3. A computed tomography system as claimed in claim 1 wherein said mechanical connection is selected from the group consisting of levers and translation mechanisms that transfers said centrifugal force acting on said mass element to said cooling liquid.

4. A computed tomography system as claimed in claim 1 wherein said compensation volume has a volume enclosure, said volume enclosure being at least partially formed by a mechanically flexible membrane that is impermeable to said cooling liquid.

5. A computed tomography system as claimed in claim 1 wherein said compensation volume is formed by a cylinder having a piston movable therein, said piston being mechanically connected to said mass element and said piston being displaced by said centrifugal force acting on said mass element.

6. A computed tomography system as claimed in claim 5 comprising a sight glass in which said cylinder is located, said sight glass comprising an indicator, selected from the group consisting of a marking and a marking range, that indicates a correct filling of said cooling liquid, said indicator being located within a movement range of said piston.

7. A computed tomography system as claimed in claim 1 comprising an elastic element that exerts pressure on said compensation volume.

8. A computed tomography system as claimed in claim 7 wherein said elastic element exerts force on said mass element.

9. A computed tomography system as claimed in claim 1 comprising a sensor that reacts to a change in fluid level of said fluid volume.

10. A computed tomography system as claimed in claim 1 comprising a ventilation device in which said compensation volume is located, said compensation volume being located closer to said system axis than other point in said fluid volume of said liquid cooling system.

11. A computed tomography system as claimed in claim 1 wherein said mass element has a higher specific density than said cooling liquid.

12. A computed tomography system as claimed in claim 1 wherein said cooling circuit comprises at least two components that are connected to said cooling circuit via couplings that automatically seal upon decoupling of said at least two components therefrom.

* * * * *